(12) United States Patent
Nagasawa et al.

(10) Patent No.: US 12,121,330 B2
(45) Date of Patent: Oct. 22, 2024

(54) ELECTROCARDIOGRAM ANALYZER AND ELECTROCARDIOGRAM ANALYSIS METHOD

(71) Applicant: NIHON KOHDEN CORPORATION, Tokyo (JP)

(72) Inventors: Masafumi Nagasawa, Tokorozawa (JP); Kazuhiro Sekikawa, Tokorozawa (JP); Kei Kimura, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 113 days.

(21) Appl. No.: 17/153,307

(22) Filed: Jan. 20, 2021

(65) Prior Publication Data

US 2021/0235999 A1    Aug. 5, 2021

(30) Foreign Application Priority Data

Jan. 30, 2020    (JP) .................................. 2020-014110

(51) Int. Cl.
| | |
|---|---|
| *A61B 5/0205* | (2006.01) |
| *A61B 5/00* | (2006.01) |
| *A61B 5/11* | (2006.01) |
| *A61B 5/363* | (2021.01) |

(52) U.S. Cl.
CPC .......... *A61B 5/0205* (2013.01); *A61B 5/1117* (2013.01); *A61B 5/1123* (2013.01); *A61B 5/363* (2021.01); *A61B 5/7221* (2013.01); *A61B 5/746* (2013.01)

(58) Field of Classification Search
CPC .................................................... A61B 5/0205
USPC ......................................................... 600/301
See application file for complete search history.

(56) References Cited

U.S. PATENT DOCUMENTS

| | | |
|---|---|---|
| 2008/0312709 A1 | 12/2008 | Volpe et al. |
| 2010/0298899 A1 | 11/2010 | Donnelly et al. |
| 2010/0312297 A1 | 12/2010 | Volpe et al. |
| 2012/0197353 A1 | 8/2012 | Donnelly et al. |
| 2014/0163334 A1 | 6/2014 | Volpe et al. |
| 2014/0221860 A1 | 8/2014 | Kimura et al. |
| 2014/0303680 A1 | 10/2014 | Donnelly et al. |
| 2016/0135706 A1* | 5/2016 | Sullivan ................. A61B 5/316 600/509 |

(Continued)

FOREIGN PATENT DOCUMENTS

| | | |
|---|---|---|
| JP | 3159276 U | 5/2010 |
| JP | 2013-530776 A | 8/2013 |

(Continued)

OTHER PUBLICATIONS

Japanese Office Action dated Sep. 20, 2023 issued in Japanese Patent Application No. 2020-014110.

*Primary Examiner* — Nicole F Lavert
(74) *Attorney, Agent, or Firm* — Pearne & Gordon LLP

(57) ABSTRACT

An electrocardiogram analyzer includes: an electrocardiogram measuring unit configured to measure an electrocardiogram based on an electrocardiographic signal of an electrode attached to a subject; a motion measuring unit configured to measure motion based on motion information of a sensor attached to the subject; and an analyzer configured to analyze occurrence of serious arrhythmia based on the electrocardiogram measured by the electrocardiogram measuring unit and the motion measured by the motion measuring unit.

19 Claims, 8 Drawing Sheets

(56) References Cited

U.S. PATENT DOCUMENTS

| | | |
|---|---|---|
| 2016/0143585 A1 | 5/2016 | Donnelly et al. |
| 2016/0278659 A1 | 9/2016 | Kaib et al. |
| 2016/0296125 A1 | 10/2016 | Volpe et al. |
| 2017/0258349 A1 | 9/2017 | Watanabe |
| 2018/0014779 A1 | 1/2018 | Donnelly et al. |
| 2018/0085588 A1* | 3/2018 | Splett .................. A61N 1/3756 |
| 2018/0110419 A1 | 4/2018 | Volpe et al. |
| 2018/0272147 A1* | 9/2018 | Freeman ................ G16H 50/30 |
| 2019/0200926 A1 | 7/2019 | Donnelly et al. |
| 2020/0253486 A1 | 8/2020 | Volpe et al. |
| 2020/0268317 A1 | 8/2020 | Donnelly et al. |
| 2021/0282652 A1 | 9/2021 | Donnelly et al. |
| 2022/0296152 A1 | 9/2022 | Volpe et al. |

FOREIGN PATENT DOCUMENTS

| | | |
|---|---|---|
| JP | 2014-150826 A | 8/2014 |
| JP | 2016-047092 A | 4/2016 |
| JP | 2017-042386 A | 3/2017 |
| WO | 2011-077097 A1 | 6/2011 |

* cited by examiner

ELECTROCARDIOGRAM ANALYZER AND ELECTROCARDIOGRAM ANALYSIS METHOD

CROSS-REFERENCE TO RELATED APPLICATIONS

This application is based on and claims priority under 35 USC 119 from Japanese Patent Application No. 2020-014110 filed on Jan. 30, 2020, the contents of which are incorporated herein by reference.

TECHNICAL FIELD

The presently disclosed subject matter relates to an electrocardiogram analyzer and an electrocardiogram analysis method.

BACKGROUND ART

An electrocardiogram analyzer in related art analyzes an electrocardiogram waveform measured from a patient in light of a predetermined arrhythmia determination criterion, and notifies a medical worker by an alarm or the like when arrhythmia is detected (see JP-A-2014-150826).

When the patient develops serious arrhythmia such as ventricular fibrillation or cardiac arrest, a heart cannot pump blood throughout a body, which may lead to a serious sequela or death.

Therefore, the medical worker needs to respond immediately to occurrence of the serious arrhythmia.

However, a patient who has left an acute phase and hospitalized in a general ward or who is undergoing rehabilitation is highly active, so an artifact (noise) caused by body movement of the patient is likely to be mixed into an electrocardiogram waveform. The electrocardiogram analyzer in the related art may erroneously determine the electrocardiogram waveform mixed with the artifact as arrhythmia and generate a false alarm.

Therefore, the electrocardiogram analyzer in the related art is equipped with countermeasures to prevent the artifact mixed in the electrocardiogram waveform from being erroneously analyzed as arrhythmia. An artifact removal filter and an artifact determination function can be exemplified as examples of such countermeasures.

However, it is not easy to accurately separate an artifact that is particularly close to a frequency component of an electrocardiogram. When the artifact is excessively removed, true arrhythmia may be erroneously removed, and a likelihood of overlooking the arrhythmia is increased.

On the other hand, when the artifact cannot be appropriately removed, a noise is determined as arrhythmia, and a false alarm is generated. Frequent false alarms reduce attention of the medical worker to alarms and slow responses of the medical worker.

As a result, a response to a patient who has truly developed serious arrhythmia may be delayed.

Therefore, the presently disclosed subject matter provides an electrocardiogram analyzer and an electrocardiogram analysis method capable of satisfying conflicting requirements of preventing arrhythmia from being overlooked (improving detection sensitivity) while reducing false detection (improving detection specificity) by changing a determination criterion of occurrence of arrhythmia in accordance with motion information of a subject.

SUMMARY

An electrocardiogram analyzer of a first aspect of the presently disclosed subject matter includes: an electrocardiogram measuring unit configured to measure an electrocardiogram based on an electrocardiographic signal of an electrode attached to a subject; a motion measuring unit configured to measure motion based on motion information of a sensor attached to the subject; and an analyzer configured to analyze occurrence of serious arrhythmia based on the electrocardiogram measured by the electrocardiogram measuring unit and the motion measured by the motion measuring unit.

An electrocardiogram analysis method of a second aspect of the presently disclosed subject matter includes: measuring an electrocardiogram based on an electrocardiographic signal of an electrode attached to a subject; measuring motion based on motion information of a sensor attached to the subject; and analyzing occurrence of serious arrhythmia based on the measured electrocardiogram and the measured motion.

BRIEF DESCRIPTION OF DRAWINGS

Exemplary embodiment(s) of the present invention will be described in detail based on the following figures, wherein.

DESCRIPTION OF EMBODIMENTS

Figure 1:
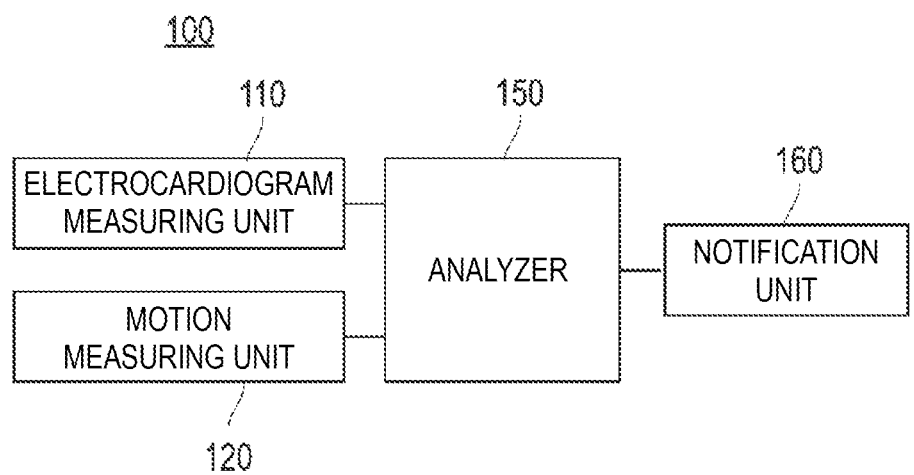
FIG. 1 is a block diagram illustrating an electrocardiogram analyzer common to Embodiments 1 to 5.
Figure 2:
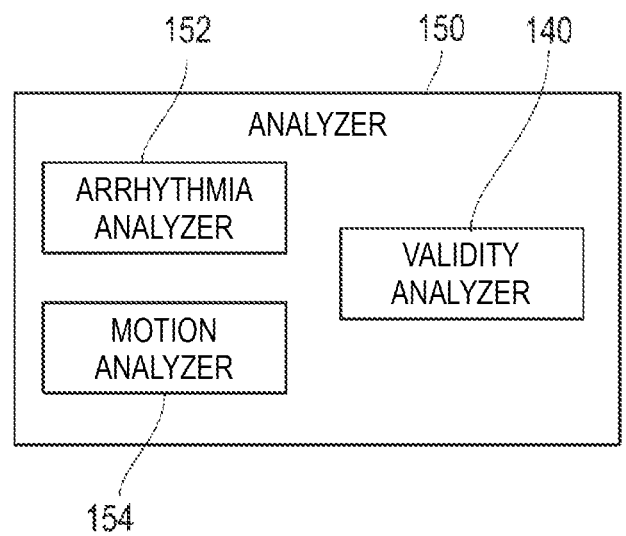
FIG. 2 is a block diagram illustrating an analyzer of FIG. 1.
Figure 3:
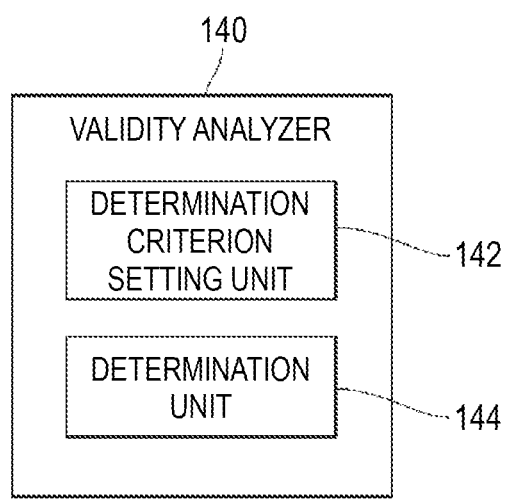
FIG. 3 is a block diagram illustrating a validity analyzer of FIG. 2.

Next, an embodiment of an electrocardiogram analyzer and an electrocardiogram analysis method of the presently disclosed subject matter will be described separately from [Embodiment 1] to [Embodiment 5] with reference to the drawings. FIGS. 1 to 3 illustrate an example of a device configuration of an electrocardiogram analyzer of the presently disclosed subject matter, which is common to Embodiments 1 to 5. FIGS. 4 to 9 illustrate an example of an operation of each of Embodiments 1 to 5 of the electrocardiogram analyzer of the presently disclosed subject matter, and an example of a procedure of each of Embodiments 1 to 5 of the electrocardiogram analysis method of the presently disclosed subject matter. It should be noted that a technical idea of the electrocardiogram analyzer and the electrocardiogram analysis method of the presently disclosed subject matter is not limited to those described in Embodiments 1 to 5 below.

Embodiment 1

(Configuration of Electrocardiogram Analyzer)

FIG. 1 is a block diagram illustrating the electrocardiogram analyzer common to Embodiments 1 to 5. As illustrated in FIG. 1, an electrocardiogram analyzer 100 can include an electrocardiogram measuring unit 110, a motion measuring unit 120, an analyzer 150, and a notification unit 160.

The electrocardiogram measuring unit 110 measures an electrocardiogram based on an electrocardiographic signal of an electrode attached to a subject. The number of the electrode attached to the subject is desirably two or more. The electrode may be attached to a body surface of the subject, or may be embedded in a body of the subject. The number of electrocardiogram waveform to be measured may be one or plural.

The motion measuring unit 120 measures motion based on motion information of a sensor attached to the subject. It is desirable to use an acceleration sensor or a gyro sensor as the sensor attached to the subject. The sensor may be directly attached to the body of the subject, may be stored in a bag or a pocket of clothing worn by the subject, or may also be embedded in the body of the subject. The sensor may be mounted integrally with the electrode attached to the subject or may be mounted integrally with a telemeter attached to the subject. By integrating the sensor with the electrode or integrating the sensor with the telemeter, the sensor can be downsized.

The sensor attached to the subject may also be any sensor other than the acceleration sensor as long as the sensor can detect the motion, activity amount and motion quantity of the subject, such as whether the subject is walking (specifically, whether the subject is walking stably or the subject is walking unstably), whether the subject is not walking, whether the subject is stopped from unstable walking, whether the subject has sat down from unstable walking, whether the subject has suddenly crouched down from walking and whether the subject has fallen down. A sensor configured by combining a plurality of types of sensors other than the acceleration sensor may also be attached to the subject so as to enable detection of such motion, activity amount and motion quantity of the subject.

The analyzer 150 analyzes occurrence of serious arrhythmia based on the electrocardiogram measured by the electrocardiogram measuring unit 110 and the motion measured by the motion measuring unit 120. Here, the serious arrhythmia is at least one of cardiac arrest, asystole, ventricular tachycardia, extreme tachycardia, and extreme bradycardia. The analyzer 150 can analyze occurrence of cardiac arrest, asystole, ventricular tachycardia, extreme tachycardia and extreme bradycardia as the serious arrhythmia. The analyzer 150 analyzes the occurrence of the serious arrhythmia at intervals of several milliseconds to several seconds, or when a heartbeat obtained from the electrocardiogram is detected. The analysis of the occurrence of the arrhythmia performed by the analyzer 150 is continuously performed in parallel with the measurement of the electrocardiogram performed by the electrocardiogram measuring unit 110 and the measurement of the motion performed by the motion measuring unit 120. The analysis unit 150 outputs an alarm signal when it is determined that it is valid to determine that the arrhythmia is serious arrhythmia as a result of the analysis of the occurrence of the arrhythmia.

When the analyzer 150 analyzes the occurrence of the serious arrhythmia, the notification unit 160 receives the alarm signal output from the analyzer 150 and outputs a sound or light to notify the occurrence of the serious arrhythmia. By providing the notification unit 160, the subject or a person around the subject, a medical worker who monitors the subject, and the like can easily know the occurrence of the serious arrhythmia.

FIG. 2 is a block diagram illustrating the analyzer of FIG. 1. As illustrated in FIG. 2, the analyzer 150 can include an arrhythmia analyzer 152, a motion analyzer 154, and a validity analyzer 140.

The arrhythmia analyzer 152 analyzes the occurrence of the arrhythmia based on the electrocardiogram measured by the electrocardiogram measuring unit 110 (see FIG. 1). The arrhythmia analyzed by the arrhythmia analyzer 152 is arrhythmia that induces ventricular fibrillation or cardiac arrest, and is, for example, at least one of cardiac arrest, asystole, ventricular tachycardia, extreme tachycardia, and extreme bradycardia.

The motion analyzer 154 analyzes a type of the motion measured by the motion measuring unit 120 (see FIG. 1). The motion analyzer 154 analyzes acceleration data output by the motion measuring unit 120, and analyzes the type of the motion based on motion data such as walking or running state, activity amount and motion quantity of the subject. For example, whether the subject is walking (specifically, whether the subject is walking stably or the subject is walking unstably), whether the subject is not walking, whether the subject is stopped from unstable walking, whether the subject has sat down from unstable walking, whether the subject has suddenly crouched down from walking and whether the subject has fallen down can be exemplified as examples of the type of the motion. Whether the subject is walking or not is determined by determining that the subject is not walking when, for example, one second has passed since detection of walking and next walking is not detected, and determining that the subject is walking when the next walking is detected within 1 second since the detection of the walking. This is because it usually takes 0.6 second per step. Therefore, if the walking is extremely slow, it is determined that the subject is not walking.

The validity analyzer 140 analyzes validity of determining that the arrhythmia is serious arrhythmia based on the type of the motion analyzed by the motion analyzer 154 when the arrhythmia analyzer 152 analyzes the occurrence of the arrhythmia. Therefore, even if the arrhythmia analyzer 152 determines that the arrhythmia has occurred, the alarm signal is not output when the validity analyzer 140 analyzes that it is not valid to determine that the arrhythmia is serious arrhythmia. On the other hand, the alarm signal is output when the validity analyzer 140 analyzes that it is valid to determine that the arrhythmia is serious arrhythmia.

FIG. 3 is a block diagram illustrating the validity analyzer of FIG. 2. As illustrated in FIG. 3, the validity analyzer 140 can include a determination criterion setting unit 142 and a determination unit 144.

The determination criterion setting unit 142 sets a determination criterion (criterion for determination) used for analyzing the validity of determining that the arrhythmia is serious arrhythmia.

Specifically, the determination criterion setting unit 142 sets a plurality of stages of detection sensitivity in accordance with the type of the motion analyzed by the motion analyzer 154 (see FIG. 2) as the determination criterion used for analyzing the validity of determining that the arrhythmia is serious arrhythmia. By providing the plurality of stages of the detection sensitivity in accordance with the type of the motion, it is possible to appropriately determine that the arrhythmia is serious arrhythmia in accordance with the type of the motion.

In Embodiment 1, detection sensitivity of a determination criterion A (medium sensitivity) is set for motion other than walking or running of the subject, and detection sensitivity of a determination criterion B (low sensitivity) is set for motion of walking or running of the subject. If the detection sensitivity is the low sensitivity, it is difficult to determine that the detected arrhythmia is serious arrhythmia. This is because it is assumed that serious arrhythmia is unlikely to occur when the subject is capable of walking or running. On the other hand, if the detection sensitivity is the medium sensitivity, it is easier to determine that the detected arrhythmia is serious arrhythmia as compared with a case where the detection sensitivity is the low sensitivity.

The determination criterion is set in such a manner that the detection sensitivity and detection specificity are well-balanced at a start of measurement. In the case of Embodiment 1, since the determination criterion A is used as a default from the start of the measurement, an optimum value is set such that the detection sensitivity and the detection specificity are well-balanced.

The determination unit 144 determines that the arrhythmia is serious arrhythmia with reference to the determination criterion set in the determination criterion setting unit 142.

In Embodiment 1, the detection sensitivity of the determination criterion A (medium sensitivity) is set for the motion other than walking or running of the subject, and the detection sensitivity of the determination criterion B (low sensitivity) is set for the motion of walking or running of the subject. The determination unit 144 determines that the arrhythmia is serious arrhythmia with reference to the determination criterion A and the determination criterion B.

(Operation of Electrocardiogram Analyzer)

Figure 4:
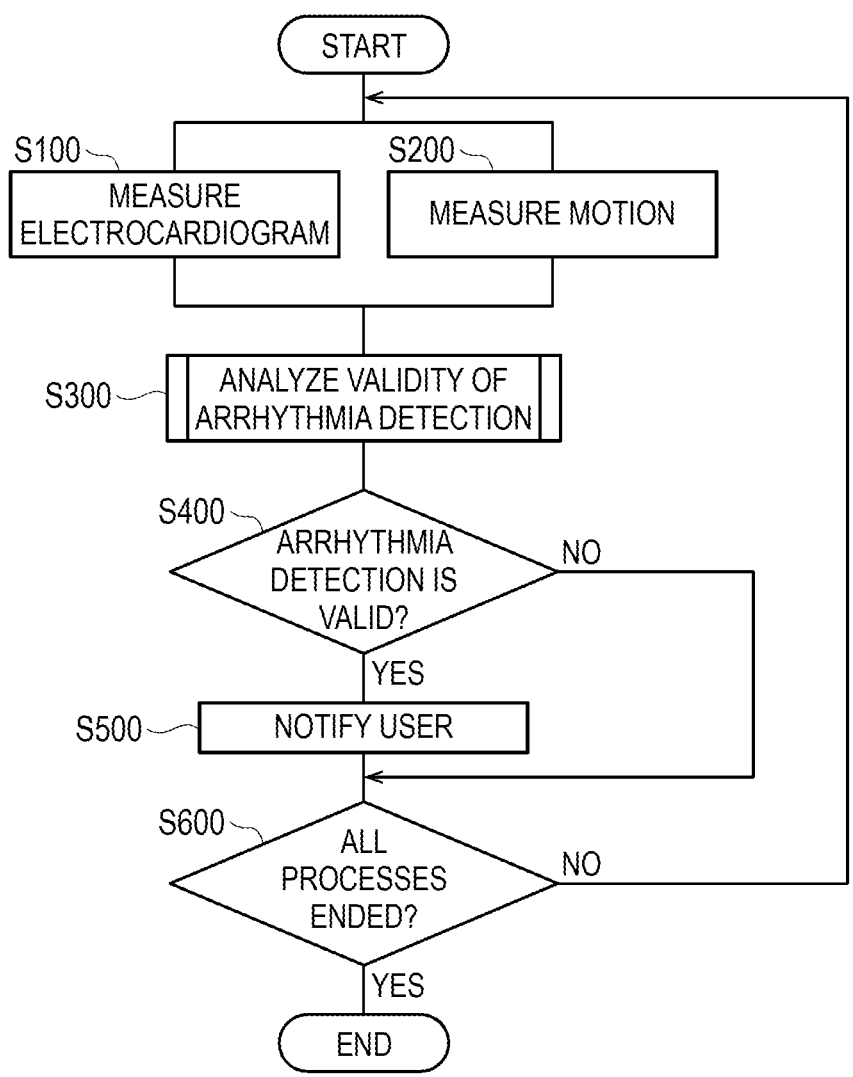
FIG. 4 is a main flowchart illustrating the electrocardiogram analyzer common to Embodiments 1 to 5 (electrocardiogram analysis method)

FIG. 4 is a main flowchart illustrating the electrocardiogram analyzer common to Embodiments 1 to 5 (electrocardiogram analysis method). Processing of the flowchart is processed at very high speed at intervals of several milliseconds to several seconds. The processing of the flowchart will be described below with reference to FIG. 1.

The electrocardiogram measuring unit 110 measures the electrocardiogram based on the electrocardiographic signal of the electrode attached to the subject (S100). Meanwhile, the motion measuring unit 120 measures the motion based on the motion information of the sensor attached to the subject (S200).

Next, the analyzer 150 analyzes the occurrence of serious arrhythmia based on the electrocardiogram measured by the electrocardiogram measuring unit 110 and the motion measured by the motion measuring unit 120. When the occurrence of the arrhythmia is analyzed, the validity of the arrhythmia detection is analyzed based on the type of the measured motion (S300).

The analyzer 150 determines whether the detection of the arrhythmia is valid (S400). When it is determined that the detection of the arrhythmia is valid (S400: YES), the notification unit 160 notifies the subject or the person around the subject, the medical worker who monitors the subject, and the like (S500). On the other hand, when it is determined that the detection of the arrhythmia is not valid (S400: NO), the process proceeds to step S600.

The analyzer 150 determines whether all processes for detecting the arrhythmia have been ended (S600). When it is determined that all the processes for detecting the arrhythmia have been ended (S600: YES), the process is ended.

When it is determined that all the processes for detecting the arrhythmia have not been ended (S600: NO), the process returns to the steps S100 and S200.

Figure 5:
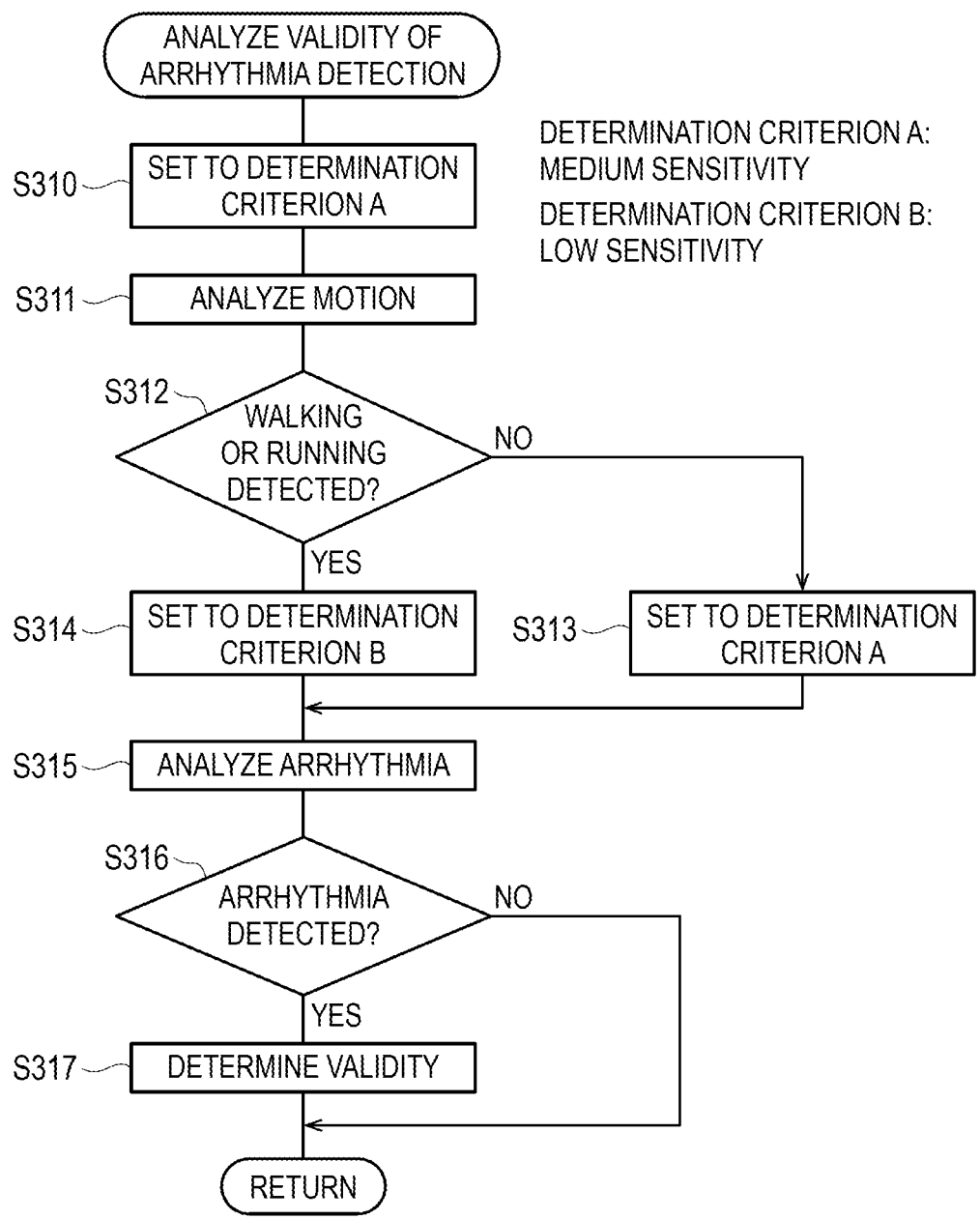
FIG. 5 is a subroutine flowchart illustrating a process of S300 (determination of validity of arrhythmia detection) of the main flowchart of FIG. 4 (Embodiment 1)

FIG. 5 is a subroutine flowchart illustrating the process of S300 (determination of validity of arrhythmia detection) of the main flowchart of FIG. 4. In Embodiment 1, the validity of the arrhythmia detection is determined by the following procedure. The processing of the flowchart will be described below with reference to FIGS. 1 to 3.

The validity analyzer 140 first sets a criterion used for determining that the arrhythmia detected by the arrhythmia analyzer 152 is serious arrhythmia to the default determination criterion A (medium sensitivity) (S310). Next, the motion analyzer 154 analyzes the motion measured by the motion measuring unit 120 (S311). The motion analyzed here is walking or running of the subject, or movement other than walking or running.

Next, it is determined whether the motion analyzer 154 has detected walking or running (S312). If the motion analyzer 154 has detected walking or running (S312: YES), the validity analyzer 140 sets the criterion used for determining that the arrhythmia detected by the arrhythmia analyzer 152 is serious arrhythmia to the determination criterion B (low sensitivity) (S314). On the other hand, if the motion analyzer 154 has not detected walking or running (S312: NO), the criterion used for determining that the arrhythmia detected by the arrhythmia analyzer 152 is serious arrhythmia is set to the determination criterion A (medium sensitivity) (S313).

The arrhythmia analyzer 152 analyzes the occurrence of the arrhythmia based on the electrocardiogram measured by the electrocardiogram measuring unit 110 (S315). Next, the arrhythmia analyzer 152 determines whether the arrhythmia is detected from the electrocardiogram measured by the electrocardiogram measuring unit 110 (S316). When the arrhythmia analyzer 152 detects the arrhythmia (S316: YES), the determination unit 144 determines the validity of the detection of the arrhythmia (S317). The validity of the detection of the arrhythmia is determined based on the determination criterion set in steps S314 and S313. On the other hand, if the arrhythmia analyzer 152 does not detect the arrhythmia (S316: NO), the process proceeds to step 400 of FIG. 4. Since the flowchart of FIG. 5 is processed at high speed, the determination criterion is changed in real time when the subject transitions from walking or running to not walking or running, or transitions inversely.

As described above, in Embodiment 1, when the subject is walking or running, the validity of the detection of the arrhythmia is determined with the low sensitivity, and when the subject is not walking or running, the validity of the detection of the arrhythmia is determined with the medium sensitivity. Therefore, in Embodiment 1, an arrhythmia alarm is more likely to be notified when the subject is not walking or running as compared with a case where the subject is walking or running.

In this way, since the determination criterion of the occurrence of the arrhythmia is changed in accordance with the motion information (whether the subject is walking or running or not walking or running) of the subject, the arrhythmia can be prevented from being overlooked while false detection of the arrhythmia can be reduced.

Embodiment 2

(Configuration of Electrocardiogram Analyzer)

The determination criterion set in the determination criterion setting unit 142 (see FIG. 3) of the electrocardiogram analyzer 100 of Embodiment 2 is different from the determination criterion setting unit 142 of Embodiment 1, while configurations other than the determination criterion setting unit 142 are the same as those of the electrocardiogram analyzer 100 of Embodiment 1.

The determination criterion setting unit 142 of Embodiment 2 sets the determination criterion used for analyzing the validity of determining that the arrhythmia is serious arrhythmia as follows. As the determination criterion, detection sensitivity of a determination criterion C (high sensitivity) is set for motion of falling down of the subject, the detection sensitivity of the determination criterion B (low sensitivity) is set for the motion of walking or running of the subject, and the detection sensitivity of the determination criterion A (medium sensitivity) is set for motion other than walking or running and falling down of the subject.

If the detection sensitivity is lower sensitivity, it is difficult to determine that the detected arrhythmia is serious arrhythmia. On the other hand, if the detection sensitivity is higher sensitivity, it is easier to determine that the detected arrhythmia is serious arrhythmia as compared with a case where the detection sensitivity is the lower sensitivity. The determination criterion is set in such a manner that the detection sensitivity and the detection specificity are well-balanced at the start of the measurement. In the case of Embodiment 2, since the determination criterion A is used as the default from the start of the measurement, the optimum value is set such that the detection sensitivity and the detection specificity are well-balanced.

The determination unit 144 determines that the arrhythmia is serious arrhythmia with reference to the determination criterion set in the determination criterion setting unit 142.

In the case of Embodiment 2, the detection sensitivity of the determination criterion C (high sensitivity) is set for the motion of falling down of the subject, the detection sensitivity of the determination criterion A (medium sensitivity) is set for the motion other than walking or running and falling down of the subject, and the detection sensitivity of the determination criterion B (low sensitivity) is set for the motion of walking or running of the subject, so that the determination unit 144 can appropriately determine that the arrhythmia is serious arrhythmia in response to each motion with reference to the determination criterion A, the determination criterion B and the determination criterion C.

(Operation of Electrocardiogram Analyzer)

Figure 6:
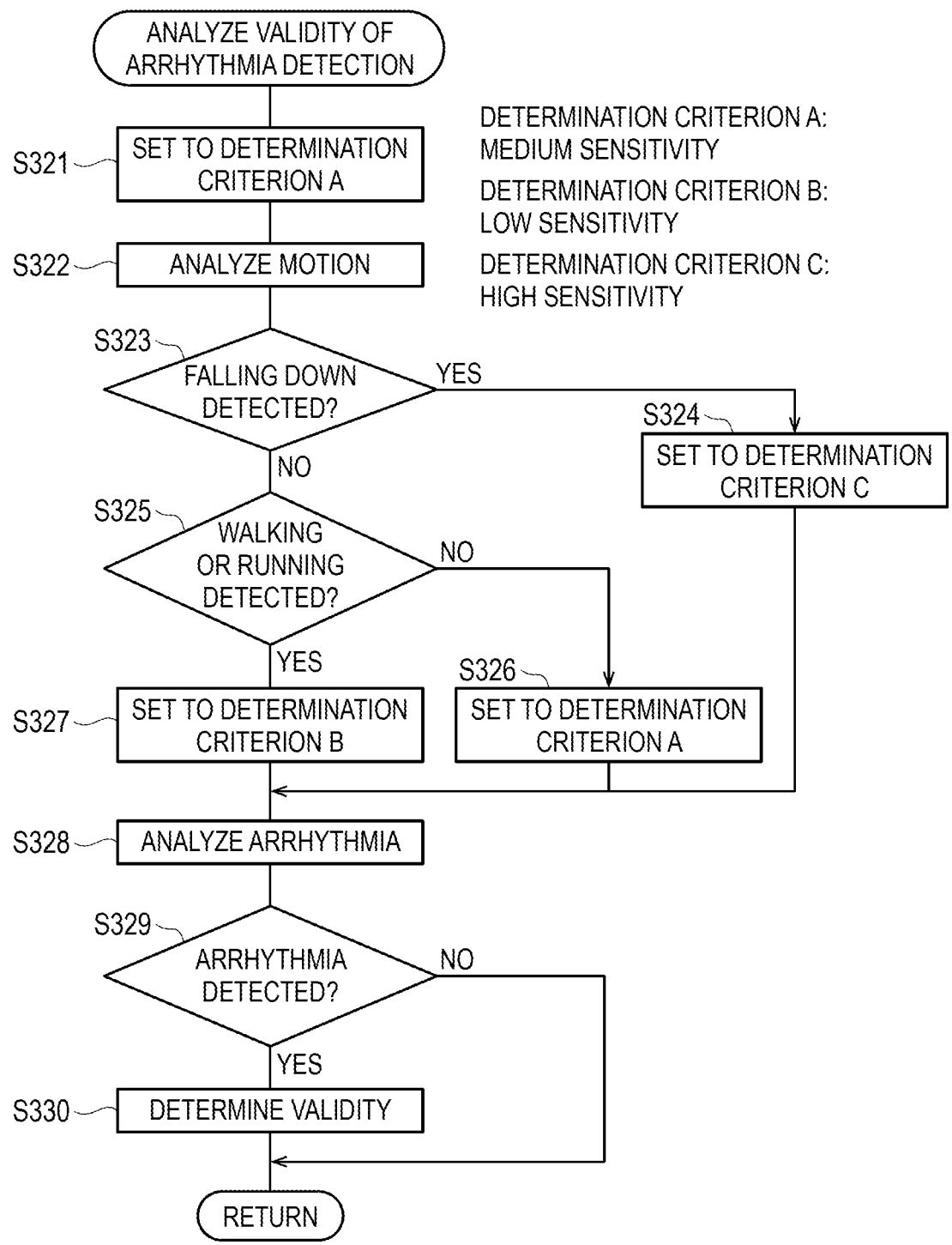
FIG. 6 is a subroutine flowchart illustrating the process of S300 (determination of validity of arrhythmia detection) of the main flowchart of FIG. 4 (Embodiment 2)

FIG. 6 is a subroutine flowchart illustrating the process of S300 (determination of validity of arrhythmia detection) of the main flowchart of FIG. 4. In Embodiment 2, the validity of the arrhythmia detection is determined by the following procedure. Processing of the flowchart will be described below with reference to FIGS. 1 to 3.

The validity analyzer 140 first sets the criterion used for determining that the arrhythmia detected by the arrhythmia analyzer 152 is serious arrhythmia to the default determination criterion A (medium sensitivity) (S321). Next, the motion analyzer 154 analyzes the motion measured by the motion measuring unit 120 (S322). The motion analyzed here is falling down of the subject, walking or running of the subject, or movement other than walking or running and falling down.

Next, it is determined whether the motion analyzer 154 has detected falling down (S323). If the motion analyzer 154 has detected falling down (S323: YES), the validity analyzer 140 sets the criterion used for determining that the arrhythmia detected by the arrhythmia analyzer 152 is serious arrhythmia to the determination criterion C (high sensitivity) (S324). When the motion analyzer 154 detects falling down, the determination criterion C (high sensitivity) may be set after notifying the subject or the person around the subject, the medical worker that monitors the subject, or the like of the falling down. On the other hand, if the motion analyzer 154 has not detected falling down (S323: NO), the motion analyzer 154 then determines whether walking or running is detected (S325).

If the motion analyzer 154 has detected walking or running (S325: YES), the validity analyzer 140 sets the criterion used for determining that the arrhythmia detected by the arrhythmia analyzer 152 is serious arrhythmia to the determination criterion B (low sensitivity) (S327). On the other hand, if the motion analyzer 154 has not detected walking or running (S325: NO), the criterion used for determining that the arrhythmia detected by the arrhythmia analyzer 152 is serious arrhythmia is set to the determination criterion A (medium sensitivity) (S326).

The arrhythmia analyzer 152 analyzes the occurrence of the arrhythmia based on the electrocardiogram measured by the electrocardiogram measuring unit 110 (S328). Next, the arrhythmia analyzer 152 determines whether the arrhythmia is detected from the electrocardiogram measured by the electrocardiogram measuring unit 110 (S329). When the arrhythmia analyzer 152 detects the arrhythmia (S329: YES), the determination unit 144 determines the validity of the detection of the arrhythmia (S330). The validity of the detection of the arrhythmia is determined based on the determination criterion set in steps S324, S326 and S327. On the other hand, if the arrhythmia analyzer 152 does not detect the arrhythmia (S329: NO), the process proceeds to step 400 of FIG. 4.

Since the flowchart of FIG. 6 is processed at high speed, the determination criterion is changed in real time each time upon detecting any movement when the subject has fallen down, when the subject is walking or running, or when the subject performs any movement other than walking or running and falling down.

Therefore, the determination criterion setting unit 142 sets the detection sensitivity to the determination criterion A (low sensitivity) when the type of the motion analyzed by the motion analyzer 154 becomes walking or running after the detection sensitivity is set to the determination criterion C (high sensitivity) when the type of the analyzed motion is falling down. Therefore, it is possible to appropriately determine that the arrhythmia is serious arrhythmia in accordance with changes in the motion.

As described above, in Embodiment 2, when the subject falls down, the validity of the detection of the arrhythmia is determined with the high sensitivity, when the subject is walking or running after the falling down, the validity of the detection of the arrhythmia is determined with the low sensitivity, and when the subject is not walking or running and falling down, the validity of the detection of the arrhythmia is determined with the medium sensitivity. Therefore, in Embodiment 2, the arrhythmia alarm is most likely to be notified when the subject falls down, and the arrhythmia alarm is less likely to be notified when the subject is not walking or running and falling down, and the arrhythmia alarm is most unlikely to be notified when the subject is walking or running after falling down.

In this way, since the determination criterion of the occurrence of the arrhythmia is changed in accordance with the motion information of the subject, the arrhythmia can be prevented from being overlooked while the false detection of the arrhythmia can be reduced.

Embodiment 3

(Configuration of Electrocardiogram Analyzer)

The determination criterion set in the determination criterion setting unit 142 (see FIG. 3) of the electrocardiogram analyzer 100 of Embodiment 3 is different from the determination criterion setting unit 142 of Embodiment 1, while configurations other than the determination criterion setting unit 142 are the same as those of the electrocardiogram analyzer 100 of Embodiment 1.

The determination criterion setting unit 142 of Embodiment 3 sets the determination criterion used for analyzing the validity of determining that the arrhythmia is serious arrhythmia as follows. As the determination criterion, detection sensitivity of a determination criterion 5 (highest sensitivity) is set for a period after falling down is detected as the motion of the subject, detection sensitivity of a determination criterion 4 is set when motion of walking of the subject is stopping or sitting from unstable walking or suddenly crouching down from walking, and a determination criterion 3 is set as a default determination criterion for the subject. Further, detection sensitivity of a determination criterion 2 is set when the motion of the subject is unstable walking, and detection sensitivity of a determination criterion 1 (lowest sensitivity) is set when the motion of the subject is stable walking.

As stages of the determination criterion decrease from the determination criterion 5 toward the determination criterion 1, the detection sensitivity stepwise changes from high sensitivity to low sensitivity. If the detection sensitivity is lower sensitivity, it is difficult to determine that the detected arrhythmia is serious arrhythmia. On the other hand, if the detection sensitivity is higher sensitivity, it is easier to determine that the detected arrhythmia is serious arrhythmia as compared with the case where the detection sensitivity is the lower sensitivity.

The determination criterion is set in such a manner that the detection sensitivity and the detection specificity are well-balanced at the start of the measurement. In the case of Embodiment 3, since the determination criterion 3 is used as the default determination criterion from the start of the measurement, the optimum value is set such that the detection sensitivity and the detection specificity are well-balanced.

The determination unit 144 determines that the arrhythmia is serious arrhythmia with reference to the determination criterion set in the determination criterion setting unit 142.

In the case of Embodiment 3, the detection sensitivity of the determination criterion 5 (highest sensitivity) is set after the falling down is detected as the motion of the subject, the detection sensitivity of the determination criterion 4 is set when the motion of walking of the subject is the stopping or sitting from the unstable walking or the suddenly crouching down from the walking, the determination criterion 3 is set as the default determination criterion for the subject, the detection sensitivity of the determination criterion 2 is set when the motion of the subject is the unstable walking, and the detection sensitivity of the determination criterion 1 (lowest sensitivity) is set when the motion of the subject is the stable walking, so that the determination unit 144 can appropriately determine that the arrhythmia is serious arrhythmia in response to each motion with reference to the determination criteria 1 to 5.

(Operation of Electrocardiogram Analyzer)

Figure 7:
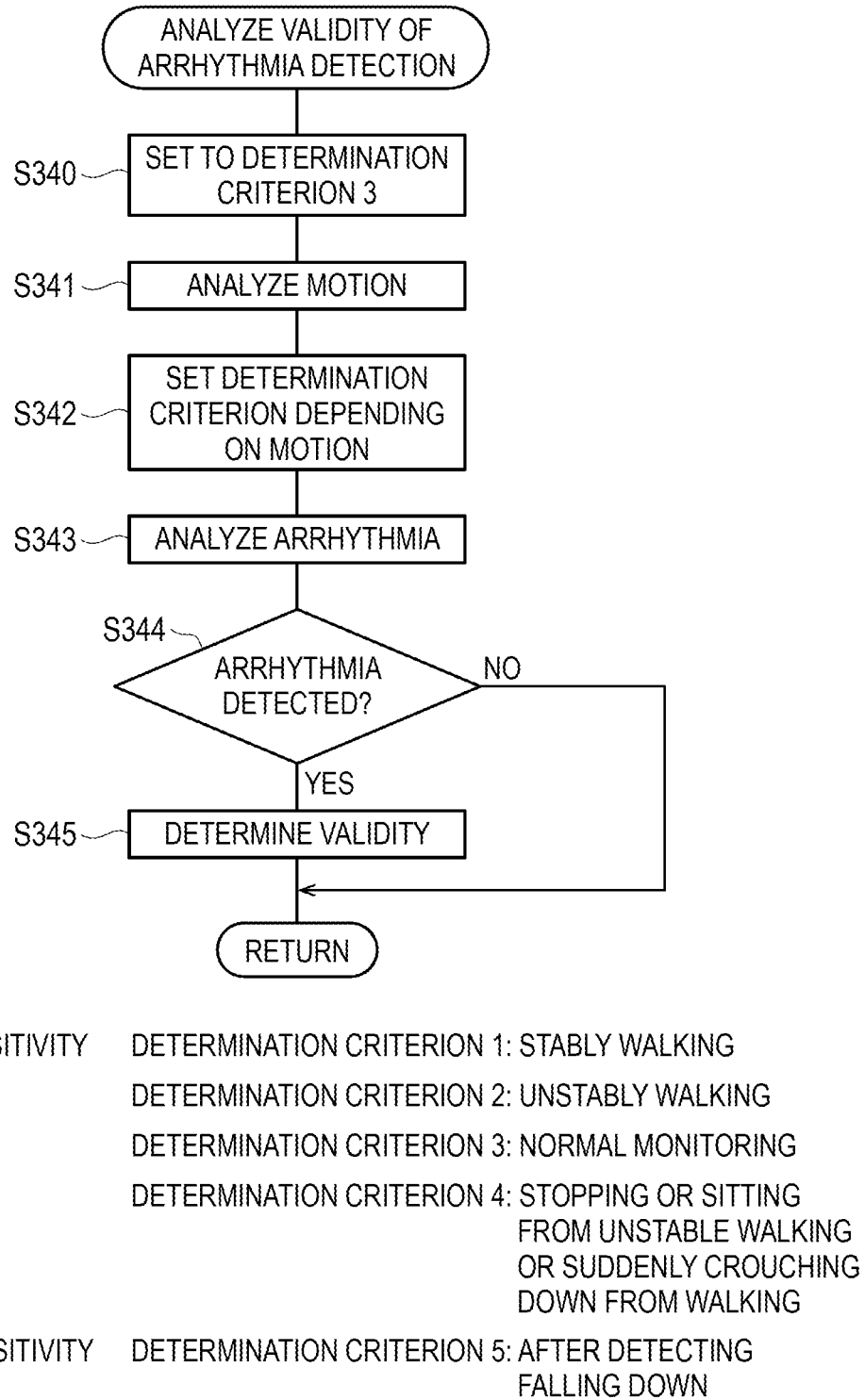
FIG. 7 is a subroutine flowchart illustrating the process of S300 (determination of validity of arrhythmia detection) of the main flowchart of FIG. 4 (Embodiment 3)

FIG. 7 is a subroutine flowchart illustrating the process of S300 (determination of validity of arrhythmia detection) of the main flowchart of FIG. 4. In Embodiment 3, the validity of the arrhythmia detection is determined by the following procedure. Processing of the flowchart will be described below with reference to FIGS. 1 to 3.

The validity analyzer 140 first sets the criterion used for determining that the arrhythmia detected by the arrhythmia analyzer 152 is serious arrhythmia to the default determination criterion 3 (normal monitoring: medium sensitivity) (S340). Next, the motion analyzer 154 analyzes the motion measured by the motion measuring unit 120 (S341). The motion analyzed here is whether the subject has fallen down, whether the subject stops or sits down from unstable walking or suddenly crouches down from walking, whether the subject is in a normal monitoring state, whether the subject is walking unstably or whether the subject is walking stably.

Next, the validity analyzer 140 sets the criterion used for determining that the arrhythmia detected by the arrhythmia analyzer 152 is serious arrhythmia based on whether the subject has fallen down, whether the subject stops or sits down from the unstable walking or suddenly crouches down from the walking, whether the subject is in the normal monitoring state, whether the subject is walking unstably and whether the subject is walking stably (S342).

Specifically, the validity analyzer 140 sets the detection sensitivity of the determination criterion 5 (highest sensitivity) if the subject has fallen down, sets the detection sensitivity of the determination criterion 4 if the subject stops or sits down from the unstable walking or suddenly crouches down from the walking, sets the detection sensitivity of the determination criterion 2 if the subject is walking unstably, sets the detection sensitivity of the determination criterion 1 (lowest sensitivity) if the subject is walking stably, and set the determination criterion 3 if the subject is doing any other motion.

The arrhythmia analyzer 152 analyzes the occurrence of the arrhythmia based on the electrocardiogram measured by the electrocardiogram measuring unit 110 (S343). Next, the arrhythmia analyzer 152 determines whether the arrhythmia is detected from the electrocardiogram measured by the electrocardiogram measuring unit 110 (S344). When the arrhythmia analyzer 152 detects the arrhythmia (S344: YES), the determination unit 144 determines the validity of the detection of the arrhythmia (S345). The validity of the detection of the arrhythmia is determined based on the determination criterion set in step S342. On the other hand, if the arrhythmia analyzer 152 does not detect the arrhythmia (S344: NO), the process proceeds to step 400 of FIG. 4.

As described above, in Embodiment 3, the validity of the detection of the arrhythmia is determined with the highest sensitivity (determination criterion 5) after the falling down of the subject, the validity of the detection of the arrhythmia is determined with slightly lowered detection sensitivity (determination criterion 4) when the subject stops or sits down from the unstable walking or suddenly crouches down from the walking, the validity of the detection of the arrhythmia is determined with the lowest detection sensitivity (determination criterion 1) when the subject is walking stably, the validity of the detection of the arrhythmia is determined with slightly risen detection sensitivity (determination criterion 2) when the subject is walking unstably, and the validity of the detection of the arrhythmia is determined with the default detection sensitivity (determination criterion 3) when the subject is doing any other motion.

Therefore, in Embodiment 3, as magnitude of the set detection sensitivity increases, the arrhythmia alarm is more likely to be notified.

In this way, since the determination criterion of the occurrence of the arrhythmia is changed in accordance with five types of the motion information of the subject, the arrhythmia can be prevented from being overlooked while the false detection of the arrhythmia can be reduced.

Embodiment 4

(Configuration of Electrocardiogram Analyzer)

The determination criterion set in the determination criterion setting unit 142 (see FIG. 3) of the electrocardiogram analyzer 100 of Embodiment 4 is different from the determination criterion setting unit 142 of Embodiment 1, while configurations other than the determination criterion setting unit 142 are the same as those of the electrocardiogram analyzer 100 of Embodiment 1.

The determination criterion setting unit 142 of Embodiment 4 sets the determination criterion used for analyzing the validity of determining that the arrhythmia is serious arrhythmia as follows. The detection sensitivity of the determination criterion is set to be higher as motion intensity of the type of the motion of the subject decreases. By setting the determination criterion in this manner, the false detection of the arrhythmia can be reduced in a case where the motion intensity is high.

Specifically, the detection sensitivity is set to low sensitivity when the type of the motion analyzed by the motion analyzer 154 is walking and a walking interval exceeds a certain range over a predetermined walking distance. The detection sensitivity is set to be lower than the low sensitivity when the type of the analyzed motion is walking and the walking interval is within the certain range over the predetermined walking distance. Further, the detection sensitivity is set to high sensitivity when the type of the motion analyzed by the motion analyzer 154 is walking and the walking is stopped when the detection sensitivity is the low sensitivity.

As described above, the detection sensitivity is set to be higher as the motion intensity of the type of the motion becomes lower, and the detection sensitivity is set to be lower as the motion intensity of the type of the motion becomes higher, so that the arrhythmia alarm can be appropriately notified without being affected by the magnitude of the motion intensity. Therefore, the arrhythmia can be prevented from being overlooked while the false detection of the arrhythmia can be reduced.

The determination criterion is set in such a manner that the detection sensitivity and the detection specificity are well-balanced at the start of the measurement. In the case of Embodiment 4, since the determination criterion A is used as the default determination criterion from the start of the measurement, the optimum value is set such that the detection sensitivity and the detection specificity are well-balanced.

The determination unit 144 determines that the arrhythmia is serious arrhythmia with reference to the determination criterion set in the determination criterion setting unit 142.

(Operation of Electrocardiogram Analyzer)

Figure 8:
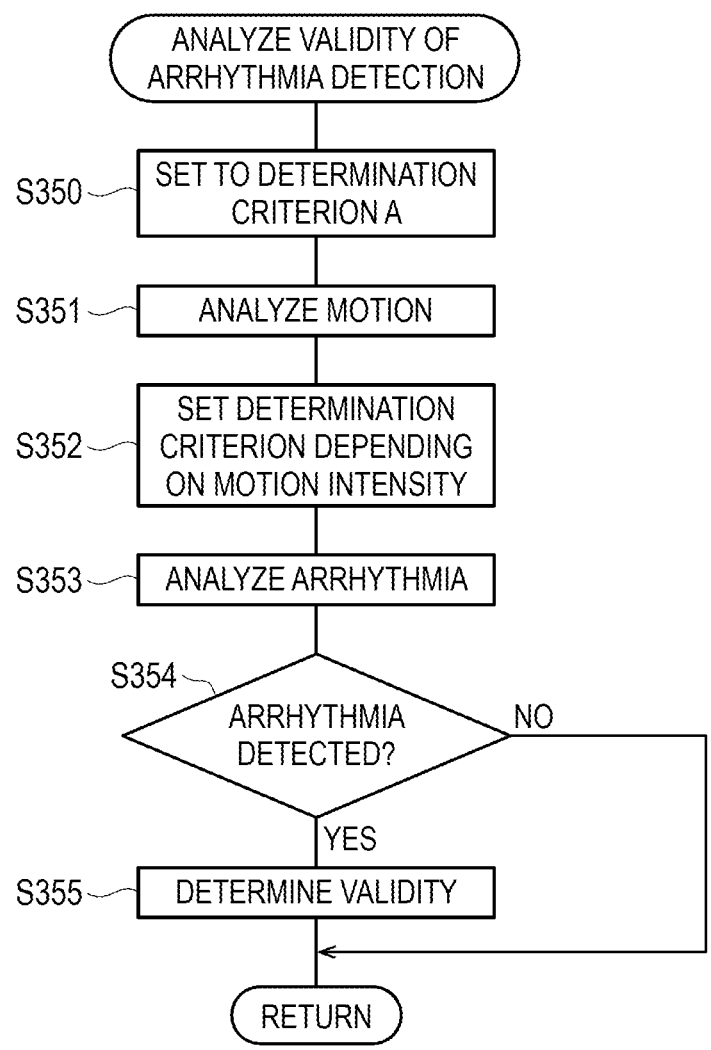
FIG. 8 is a subroutine flowchart illustrating the process of S300 (determination of validity of arrhythmia detection) of the main flowchart of FIG. 4 (Embodiment 4)

FIG. 8 is a subroutine flowchart illustrating the process of S300 (determination of validity of arrhythmia detection) of the main flowchart of FIG. 4. In Embodiment 4, the validity of the arrhythmia detection is determined by the following procedure. Processing of the flowchart will be described below with reference to FIGS. 1 to 3.

The validity analyzer 140 first sets the criterion used for determining that the arrhythmia detected by the arrhythmia analyzer 152 is serious arrhythmia to the default determination criterion A (medium sensitivity) (S350). Next, the motion analyzer 154 analyzes the motion measured by the motion measuring unit 120 (S351). The motion analyzed here is, for example, whether the walking interval exceeds the certain range over the predetermined walking distance when the subject is walking, whether the walking interval is within the certain range over the predetermined walking distance when the subject is walking, whether the walking is stopped when the subject is walking while the detection sensitivity is the low sensitivity.

Next, the validity analyzer 140 sets the criterion used for determining that the arrhythmia detected by the arrhythmia analyzer 152 is serious arrhythmia to an optimal value in accordance with whether the walking interval exceeds the certain range or whether the walking interval is within the certain range over the predetermined walking distance when the subject is walking, and whether the walking is stopped when the subject is walking while the detection sensitivity is the low sensitivity. Specifically, the detection sensitivity is set to the low sensitivity when the subject is walking and the walking interval exceeds the certain range over the predetermined walking distance. The detection sensitivity is set to be lower than the low sensitivity when the subject is walking and the walking interval is within the certain range over the predetermined walking distance. Further, the detection sensitivity is set to the high sensitivity when the subject is walking and the walking is stopped when the detection sensitivity is the low sensitivity (S352).

The arrhythmia analyzer 152 analyzes the occurrence of the arrhythmia based on the electrocardiogram measured by the electrocardiogram measuring unit 110 (S353). Next, the arrhythmia analyzer 152 determines whether the arrhythmia is detected from the electrocardiogram measured by the electrocardiogram measuring unit 110 (S354). When the arrhythmia analyzer 152 detects the arrhythmia (S354: YES), the determination unit 144 determines the validity of the detection of the arrhythmia (S355). The validity of the detection of the arrhythmia is determined based on the determination criterion set in step S352. On the other hand, if the arrhythmia analyzer 152 does not detect the arrhythmia (S354: NO), the process proceeds to step 400 of FIG. 4.

As described above, in the case of Embodiment 4, the detection sensitivity is set to be higher as the motion intensity of the type of the motion of the subject becomes lower, and conversely the detection sensitivity is set to be lower as the motion intensity of the type of the motion of the subject becomes higher, so that the determination unit 144 can appropriately determine that the arrhythmia is serious arrhythmia in accordance with the set detection sensitivity.

As described above, in Embodiment 4, since the determination criterion of the occurrence of the arrhythmia is changed in accordance with the motion information of the subject, the arrhythmia can be prevented from being overlooked while the false detection of the arrhythmia can be reduced.

Embodiment 5

(Configuration of Electrocardiogram Analyzer)

The determination criterion set in the determination criterion setting unit 142 (see FIG. 3) of the electrocardiogram analyzer 100 of Embodiment 5 is different from the determination criterion setting unit 142 of Embodiment 1. The motion analyzer 154 (see FIG. 2) analyzes the type and the motion intensity of the measured motion over time, which is also different from the motion analyzer 154 of Embodiment 1. Further, the validity analyzer 140 analyzes the validity of determining that the measured arrhythmia is serious arrhythmia based on the type and the motion intensity of the motion analyzed by tracing back and analyzing the type and the motion intensity of the motion measured before when the occurrence of the arrhythmia is analyzed, which is also different from the validity analyzer 140 of Embodiment 1. Other configurations are the same as those of the electrocardiogram analyzer 100 of Embodiment 1.

The determination criterion setting unit 142 of Embodiment 5 determines the validity of determining that the arrhythmia is serious arrhythmia as follows. For example, presence or absence of detection of walking and motion quantity are evaluated by tracing back from a time point when a possibility of ventricular fibrillation or cardiac arrest is detected, and the alarm is canceled if stable walking or moving continues. Otherwise, the alarm is output.

Specifically, the validity of the alarm is verified by determining whether the walking is continued Y times within a period divided every X seconds (for example, X=L, Y=3), whether walking speed or pace above a certain level (for example, speed of 3.2 km/hr, pace of 100 step/min) lasts for Y seconds (for example, Y=3), whether elapsed time from last walking detection is within Y seconds (for example, Y=1), whether stable moving (for example, 3.0 METs) lasts for Y seconds (for example, Y=3), and the like.

It may also be configured such that the presence or absence of the detection of the walking and the motion quantity are evaluated by tracing back from the time point when the possibility of ventricular fibrillation or cardiac arrest is detected, the alarm is held if unstable walking (speed of 1.0 to 3.1 km/hr) or weak movement (1.0 to 2.9 METs) continues, and the alarm is finally output if stable walking or movement is not detected in the following N (for example, 1) seconds.

The determination criterion is set in such a manner that the detection sensitivity and the detection specificity are well-balanced at the start of the measurement. In the case of Embodiment 5, since the determination criterion A is used as the default determination criterion from the start of the measurement, the optimum value is set such that the detection sensitivity and the detection specificity are well-balanced.

The determination unit 144 determines that the arrhythmia is serious arrhythmia with reference to the determination criterion set in the determination criterion setting unit 142.

(Operation of Electrocardiogram Analyzer)

Figure 9:
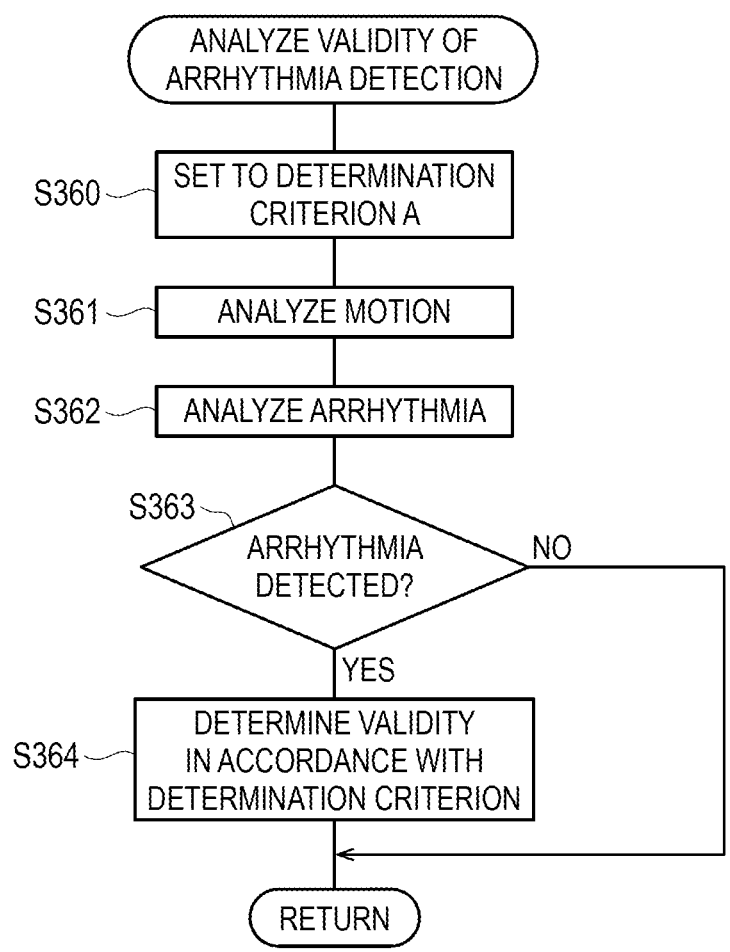
FIG. 9 is a subroutine flowchart illustrating the process of S300 (determination of validity of arrhythmia detection) of the main flowchart of FIG. 4 (Embodiment 5).

FIG. 9 is a subroutine flowchart illustrating the process of S300 (determination of validity of arrhythmia detection) of the main flowchart of FIG. 4. In Embodiment 5, the validity of the arrhythmia detection is determined by the following procedure. Processing of the flowchart will be described below with reference to FIGS. 1 to 3.

The validity analyzer 140 first sets the criterion used for determining that the arrhythmia detected by the arrhythmia analyzer 152 is serious arrhythmia to the default determination criterion A (medium sensitivity) (S360). Next, the motion analyzer 154 analyzes the motion measured by the motion measuring unit 120 (S361).

The motion analyzed here are the presence or absence of the detection of the walking and motion quantity traced back from the time point when the possibility of ventricular fibrillation or cardiac arrest is detected. Specifically, the motion is whether the walking is continued Y times within the period divided every X seconds, whether the walking speed or pace above the certain level lasts for Y seconds, whether the elapsed time from last walking detection is within Y seconds, whether the stable movement lasts for Y seconds, whether the unstable walking or weak movement is continued, whether the stable walking or movement is detected in the following N seconds, and the like.

The arrhythmia analyzer 152 analyzes the occurrence of the arrhythmia based on the electrocardiogram measured by the electrocardiogram measuring unit 110 (S362). Next, the arrhythmia analyzer 152 determines whether the arrhythmia is detected from the electrocardiogram measured by the electrocardiogram measuring unit 110 (S363). When the arrhythmia analyzer 152 detects the arrhythmia (S33: YES), the determination unit 144 compares the motion analyzed in step S361 with the determination criterion and determines the validity of the detection of the arrhythmia (S364). On the other hand, if the arrhythmia analyzer 152 does not detect the arrhythmia (S363: NO), the process proceeds to step 400 of FIG. 4.

As described above, in Embodiment 5, the presence or absence of the detection of the walking and the motion quantity are evaluated by tracing back from the time point when the possibility of ventricular fibrillation or cardiac arrest is detected, the alarm is canceled if the stable walking or moving continues, and otherwise the alarm is output, so that the arrhythmia can be prevented from being overlooked while the false detection of the arrhythmia can be reduced.

The electrocardiogram analyzer and the electrocardiogram analysis method of the presently disclosed subject matter have been described above separately from Embodiment 1 to Embodiment 5. However, a technical scope of the electrocardiogram analyzer and the electrocardiogram analysis method of the presently disclosed subject matter is not limited to the range described in the embodiments. It goes without saying that an invention having the same technical idea as the presently disclosed subject matter is included in the technical scope of the presently disclosed subject matter.

First to third levels may be set to the determination criterion setting unit 142 depending on a type of analyzed motion of a subject. For example, the detection criterion may be set as a third level (low sensitivity) when the type of the analyzed motion is walking or running, the detection criterion may be set as a first level (high sensitivity) when the type of the analyzed motion is falling down, and the detection criterion may be set as a second level (medium sensitivity) when the type of the analyzed motion is motion other than walking, running and falling down.

The aforementioned embodiments are summarized as follows.

An electrocardiogram analyzer of a first aspect of the presently disclosed subject matter includes: an electrocardiogram measuring unit configured to measure an electrocardiogram based on an electrocardiographic signal of an electrode attached to a subject; a motion measuring unit configured to measure motion based on motion information of a sensor attached to the subject; and an analyzer configured to analyze occurrence of serious arrhythmia based on the electrocardiogram measured by the electrocardiogram measuring unit and the motion measured by the motion measuring unit.

An electrocardiogram analysis method of a second aspect of the presently disclosed subject matter includes: measuring an electrocardiogram based on an electrocardiographic signal of an electrode attached to a subject; measuring motion based on motion information of a sensor attached to the subject; and analyzing occurrence of serious arrhythmia based on the measured electrocardiogram and the measured motion.

According to the electrocardiogram analyzer and the electrocardiogram analysis method of the presently disclosed subject matter, since the occurrence of serious arrhythmia is analyzed based on the electrocardiogram and the motion, the conflicting requirements of preventing the arrhythmia from being overlooked (improving detection sensitivity) while reducing the false detection (improving detection specificity) can be satisfied.

What is claimed is:

1. An electrocardiogram analyzer comprising:
   an electrocardiogram measuring unit configured to measure an electrocardiogram based on an electrocardiographic signal of an electrode attached to an outside of a body of a subject;
   a motion measuring unit configured to measure body motion based on body motion information of a sensor attached to the outside of the body of the subject;
   an analyzer configured to analyze occurrence of serious arrhythmia based on the electrocardiogram measured by the electrocardiogram measuring unit and the body motion measured by the motion measuring unit;
   an arrhythmia analyzer configured to analyze occurrence of arrhythmia based on the measured electrocardiogram;
   a motion analyzer configured to analyze a type of the measured body motion; and
   a validity analyzer configured to analyze validity of determining that the arrhythmia is serious arrhythmia based on the type of the body motion when the occurrence of the arrhythmia is analyzed.

2. The electrocardiogram analyzer according to claim 1, wherein the validity analyzer includes:
   a determination criterion setting unit configured to set a determination criterion used for analyzing the validity of determining that the arrhythmia is serious arrhythmia; and
   a determination unit configured to determine that the arrhythmia is serious arrhythmia with reference to the determination criterion.

3. The electrocardiogram analyzer according to claim 2, wherein the determination criterion setting unit is configured to set a plurality of stages of detection sensitivity in accordance with the type of the analyzed body motion as the determination criterion used for analyzing the validity of determining that the arrhythmia is serious arrhythmia.

4. The electrocardiogram analyzer according to claim 3, wherein the determination criterion setting unit is configured to set the detection sensitivity to low sensitivity when the type of the analyzed body motion is walking or running, set the detection sensitivity to high sensitivity when the type of the analyzed body motion is falling down, and set the detection sensitivity to medium sensitivity when the type of the analyzed body motion is other than walking or running and falling down.

5. The electrocardiogram analyzer according to claim 4, wherein the determination criterion setting unit is configured to set the detection sensitivity to the medium sensitivity when the type of the analyzed body motion becomes walking or running after the detection sensitivity is set to the high sensitivity when the type of the analyzed body motion is falling down.

6. The electrocardiogram analyzer according to claim 3, wherein the determination criterion setting unit is configured to set the detection sensitivity to low sensitivity when the type of the analyzed body motion is walking and a walking interval is not within a certain range over a predetermined walking distance.

7. The electrocardiogram analyzer according to claim 6, wherein the determination criterion setting unit is configured to set the detection sensitivity to be lower than the low sensitivity when the type of the analyzed body motion is walking and the walking interval is within the certain range over the predetermined walking distance.

8. The electrocardiogram analyzer according to claim 6, wherein the determination criterion setting unit is configured to set the detection sensitivity to high sensitivity when the type of the analyzed body motion is walking and the walking is stopped when the detection sensitivity is the low sensitivity.

9. The electrocardiogram analyzer according to claim 3, wherein the determination criterion setting unit is configured to set the detection sensitivity to medium sensitivity when the type of the analyzed body motion is other than walking or running and falling down.

10. The electrocardiogram analyzer according to claim 3, wherein the determination criterion setting unit is configured to set the detection sensitivity to high sensitivity when the type of the analyzed body motion is falling down.

11. The electrocardiogram analyzer according to claim 3, wherein the determination criterion setting unit is configured to set the detection sensitivity higher as motion intensity of the type of the analyzed body motion becomes lower.

12. The electrocardiogram analyzer according to claim 1, wherein
    the motion analyzer is configured to analyze a motion intensity of the measured body motion over time; and
    the validity analyzer is configured to analyze validity of determining that the measured arrhythmia is serious arrhythmia based on a motion intensity of motion obtained by tracing back and analyzing motion intensity of motion measured when the occurrence of the arrhythmia is analyzed.

13. The electrocardiogram analyzer according to claim 1, further comprising:
    a notification unit configured to notify the occurrence of serious arrhythmia when the analyzer analyzes that the serious arrhythmia has occurred.

14. The electrocardiogram analyzer according to claim 1, wherein the sensor is mounted integrally with the electrode attached to the subject or mounted integrally with a telemeter attached to the subject.

15. The electrocardiogram analyzer according to claim 1, wherein the serious arrhythmia is at least one of cardiac arrest, asystole, ventricular tachycardia, extreme tachycardia, and extreme bradycardia.

16. The electrocardiogram analyzer according to claim 1, wherein the body motion is an activity performed by the subject.

17. The electrocardiogram analyzer according to claim 1, wherein the body motion information includes information as to at least one of whether or not the subject is walking, whether the subject has sat down, whether the subject has crouched down, or whether the subject has fallen down.

18. An electrocardiogram analysis method comprising:
    measuring an electrocardiogram based on an electrocardiographic signal of an electrode attached to an outside of a body of a subject;

measuring body motion based on body motion information of a sensor attached to the outside of the body of the subject;

analyzing occurrence of serious arrhythmia based on the measured electrocardiogram and the measured body motion;

analyzing a type of the measured body motion; and analyzing validity of determining that the arrhythmia is serious arrhythmia based on the type of the body motion when the occurrence of the arrhythmia is analyzed.

19. An electrocardiogram analyzer comprising:

an electrocardiogram measuring unit configured to measure an electrocardiogram based on an electrocardiographic signal of an electrode attached to an outside of a body of a subject;

a motion measuring unit configured to measure body motion based on body motion information of a sensor attached to the outside of the body of the subject; and an analyzer configured to analyze an occurrence of serious arrhythmia based on the electrocardiogram measured by the electrocardiogram measuring unit and the body motion measured by the motion measuring unit;

an arrhythmia analyzer configured to analyze occurrence of arrhythmia based on the measured electrocardiogram;

a motion analyzer configured to analyze a type of the measured body motion; and a validity analyzer configured to analyze validity of determining that the arrhythmia is serious arrhythmia based on the type of the body motion when the occurrence of the arrhythmia is analyzed, wherein the serious arrhythmia is at least one of cardiac arrest, asystole, ventricular tachycardia, extreme tachycardia, or extreme bradycardia.

* * * * *

UNITED STATES PATENT AND TRADEMARK OFFICE
CERTIFICATE OF CORRECTION

| | | |
|---|---|---|
| PATENT NO. | : 12,121,330 B2 | Page 1 of 1 |
| APPLICATION NO. | : 17/153307 | |
| DATED | : October 22, 2024 | |
| INVENTOR(S) | : Masafumi Nagasawa et al. | |

It is certified that error appears in the above-identified patent and that said Letters Patent is hereby corrected as shown below:

In the Claims

Column 16; Line 40:
"and analyzing motion intensity" should be --and analyzing the motion intensity--.

Signed and Sealed this
Third Day of June, 2025

Coke Morgan Stewart
*Acting Director of the United States Patent and Trademark Office*